(12) United States Patent
Kashiwagi et al.

(10) Patent No.: US 10,624,560 B2
(45) Date of Patent: Apr. 21, 2020

(54) ELECTRONIC DEVICE, AND ELECTRONIC DEVICE CONTROL METHOD

(71) Applicant: SHARP KABUSHIKI KAISHA, Sakai, Osaka (JP)

(72) Inventors: Tohru Kashiwagi, Sakai (JP); Michiaki Satou, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 257 days.

(21) Appl. No.: 15/570,264

(22) PCT Filed: Apr. 18, 2016

(86) PCT No.: PCT/JP2016/062269
§ 371 (c)(1),
(2) Date: Oct. 27, 2017

(87) PCT Pub. No.: WO2016/175078
PCT Pub. Date: Nov. 3, 2016

(65) Prior Publication Data
US 2018/0132762 A1    May 17, 2018

(30) Foreign Application Priority Data

Apr. 28, 2015    (JP) .................................. 2015-092312

(51) Int. Cl.
*H04W 4/40* (2018.01)
*A61B 5/11* (2006.01)
(Continued)

(52) U.S. Cl.
CPC .............. *A61B 5/1118* (2013.01); *A61B 5/11* (2013.01); *G01C 21/165* (2013.01);
(Continued)

(58) Field of Classification Search
CPC ........ A61B 5/1118; A61B 5/11; A61B 5/1112; A61B 5/1123; H04W 4/02; H04W 4/40;
(Continued)

(56) References Cited

U.S. PATENT DOCUMENTS

2012/0059623 A1    3/2012    Sambongi
2016/0306338 A1    10/2016   Morita

FOREIGN PATENT DOCUMENTS

JP    2003-156361 A    5/2003
JP    2006-242578 A    9/2006
(Continued)

OTHER PUBLICATIONS

Shin et al., Adaptive Step Length Estimation Algorithm Using Low-Cost MEMS Inertial Sensors, Feb. 6-8, 2007, SAS 2007—IEEE Sensors Applications Symposium, San Diego, California, 5 pp. (Year: 2007).*

*Primary Examiner* — Toan M Le
(74) *Attorney, Agent, or Firm* — ScienBiziP, P.C.

(57) ABSTRACT

An electronic device (1) includes: a positional information obtaining section (21) for obtaining positional information; a boarding determining section (12) for determining whether or not a user has boarded or exited a vehicle; and a frequency switching section (14) for switching a frequency, at which the positional information is obtained, from a first frequency to a second frequency in a case where it is determined that the user has boarded or exited the vehicle.

5 Claims, 5 Drawing Sheets

(51) Int. Cl.
  *G01C 22/00* (2006.01)
  *H04W 4/02* (2018.01)
  *G01S 19/34* (2010.01)
  *G01C 21/16* (2006.01)
  *G01S 19/48* (2010.01)

(52) U.S. Cl.
  CPC ............ *G01C 22/006* (2013.01); *G01S 19/34* (2013.01); *G01S 19/48* (2013.01); *H04W 4/02* (2013.01); *H04W 4/40* (2018.02); *A61B 5/1112* (2013.01); *A61B 5/1123* (2013.01); *A61B 2503/12* (2013.01)

(58) Field of Classification Search
  CPC ....... G01S 19/34; G01S 19/48; G01C 22/006; G01C 21/165
  See application file for complete search history.

(56) References Cited

FOREIGN PATENT DOCUMENTS

| | | |
|---|---|---|
| JP | 2012-052936 A | 3/2012 |
| JP | 2015-088905 A | 5/2015 |

* cited by examiner

ELECTRONIC DEVICE, AND ELECTRONIC DEVICE CONTROL METHOD

TECHNICAL FIELD

The present invention relates to an electronic device for obtaining positional information, and a control program for obtaining the positional information.

BACKGROUND ART

Conventionally, there is known a technique of detecting the number of steps taken by a user and notifying the user of the number. For example, Patent Literature 1 discloses a technique in which the number of steps taken by a user is counted on the basis of a result of detection by a Z axis sensor for detecting a horizontal oscillation, and in a case where it is determined, on the basis of an acceleration detected by an X-Y axis sensor for detecting a horizontal acceleration, that the user is traveling on board a vehicle, measurement of the number of steps is masked.

Further, in general, in an electronic device which obtains positional information of a traveling user and notifies the user of a position of the user, timing for obtaining the positional information of the user can be set by detecting, in accordance with a conventional technique as described above, the number of steps taken by the user and using thus detected number.

CITATION LIST

Patent Literature

[Patent Literature 1]
Japanese Patent Application Publication, Tokukai, No. 2003-156361 A (Publication Date: May 30, 2003)

SUMMARY OF INVENTION

Technical Problem

However, there are problems in setting the timing for obtaining the positional information of the user with use of the detected number of steps taken by the user. One problem is that in a case where the timing is set to every small number of steps, the electronic device obtains the positional information too frequently, so that power consumption of the electronic device increases. Another problem is that since the user walks less while on board a vehicle, setting the timing to every large number of steps may prevent the electronic device from accurately measuring a position at which the user exits the vehicle, in a case where the user exits the vehicle.

The present invention is accomplished in view of the foregoing problems. An object of the present invention is to provide an electronic device which not only is capable of measuring an accurate position of a user when the user exits a vehicle but also achieves a reduction in power consumption.

Solution to Problem

In order to attain the object, an electronic device in accordance with one aspect of the present invention is an electronic device including: a positional information obtaining section for obtaining positional information of a user; a boarding determining section for determining whether or not the user has boarded or exited a vehicle; and a frequency switching section for switching a frequency, at which the positional information obtaining section obtains the positional information, from a first frequency to a second frequency in a case where the boarding determining section determines that the user has boarded or exited the vehicle, the first frequency being a frequency which had been set before the user boarded the vehicle.

In order to attain the object, a method., in accordance with one aspect of the present invention, for controlling an electronic device is a method for controlling an electronic device, including the steps of: (a) obtaining positional information of a user; (b) determining whether or not the user has boarded or exited a vehicle; and (c) switching, in a case where it is determined in the step (b) that the user has boarded or exited the vehicle, a frequency, at which the positional information is obtained in the step (a), from a first frequency to a second frequency, the first frequency being a frequency which had been set before the user boarded the vehicle.

Advantageous Effects of Invention

According to one aspect of the present invention, it is possible to provide an electronic device which not only is capable of measuring an accurate position of a user when the user exits a vehicle but also achieves a reduction in power consumption.

BRIEF DESCRIPTION OF DRAWINGS

(a) and (b) of FIG. 2 are views each for explaining an overview of position measurement carried out by the electronic device.

DESCRIPTION OF EMBODIMENTS

The following description will discuss in detail embodiments of the present invention. For easy explanation, the same reference signs will be given to members each having the same function as a member illustrated in the embodiments, and descriptions on such a member will be omitted.

[Embodiment 1]

Figure 1:
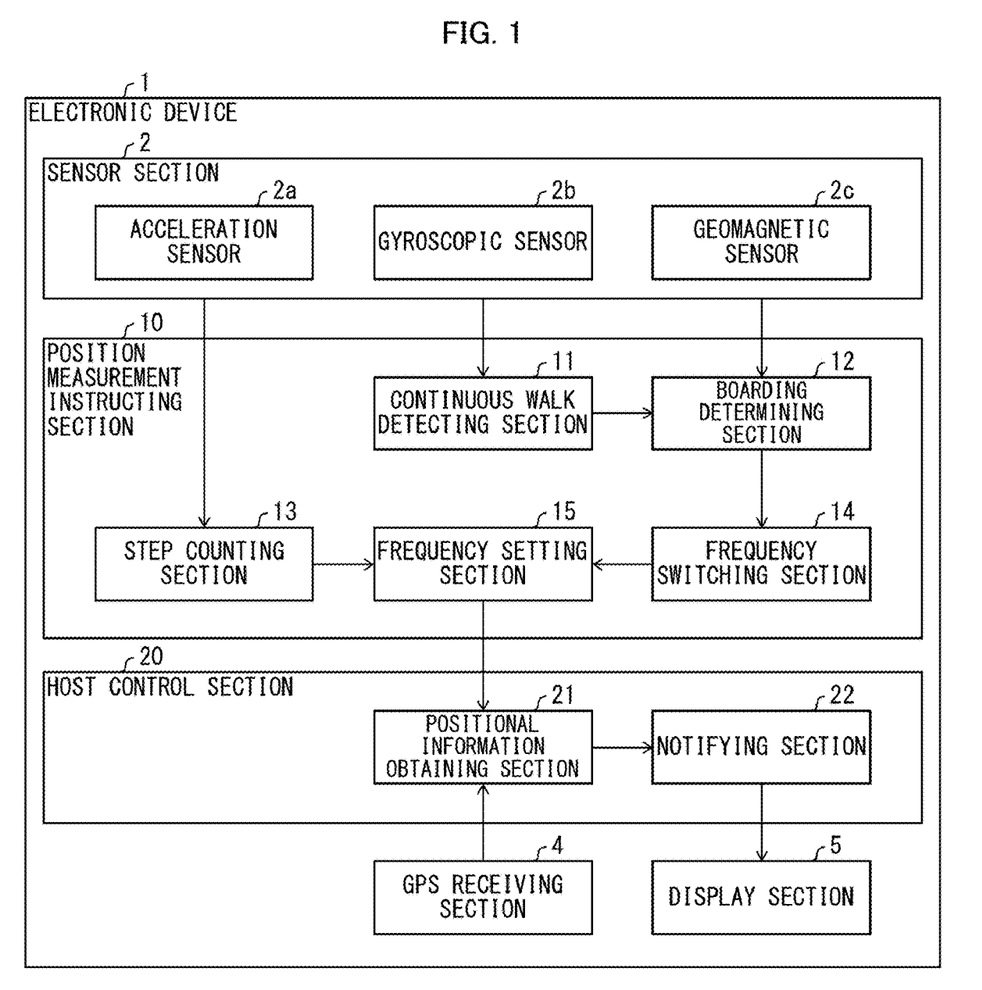
FIG. 1 is a functional block diagram schematically illustrating a configuration of an electronic device in accordance with. Embodiment 1 of the present invention.
Figure 2:
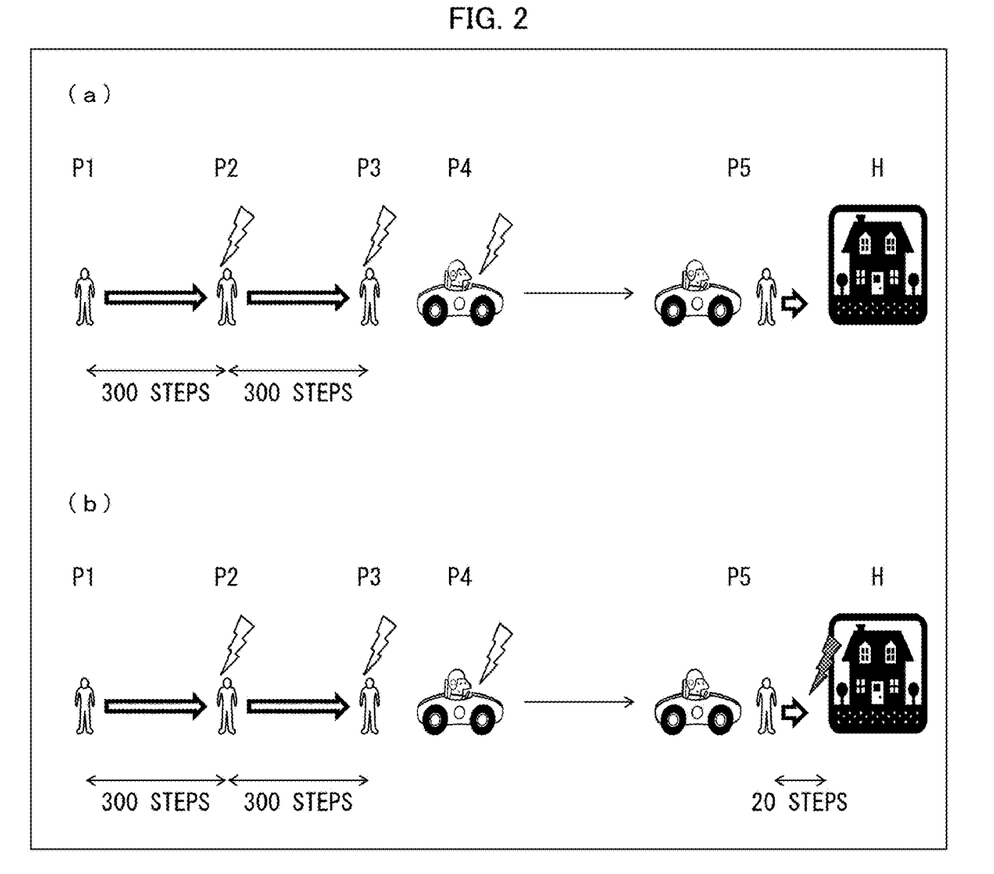
Figure 3:
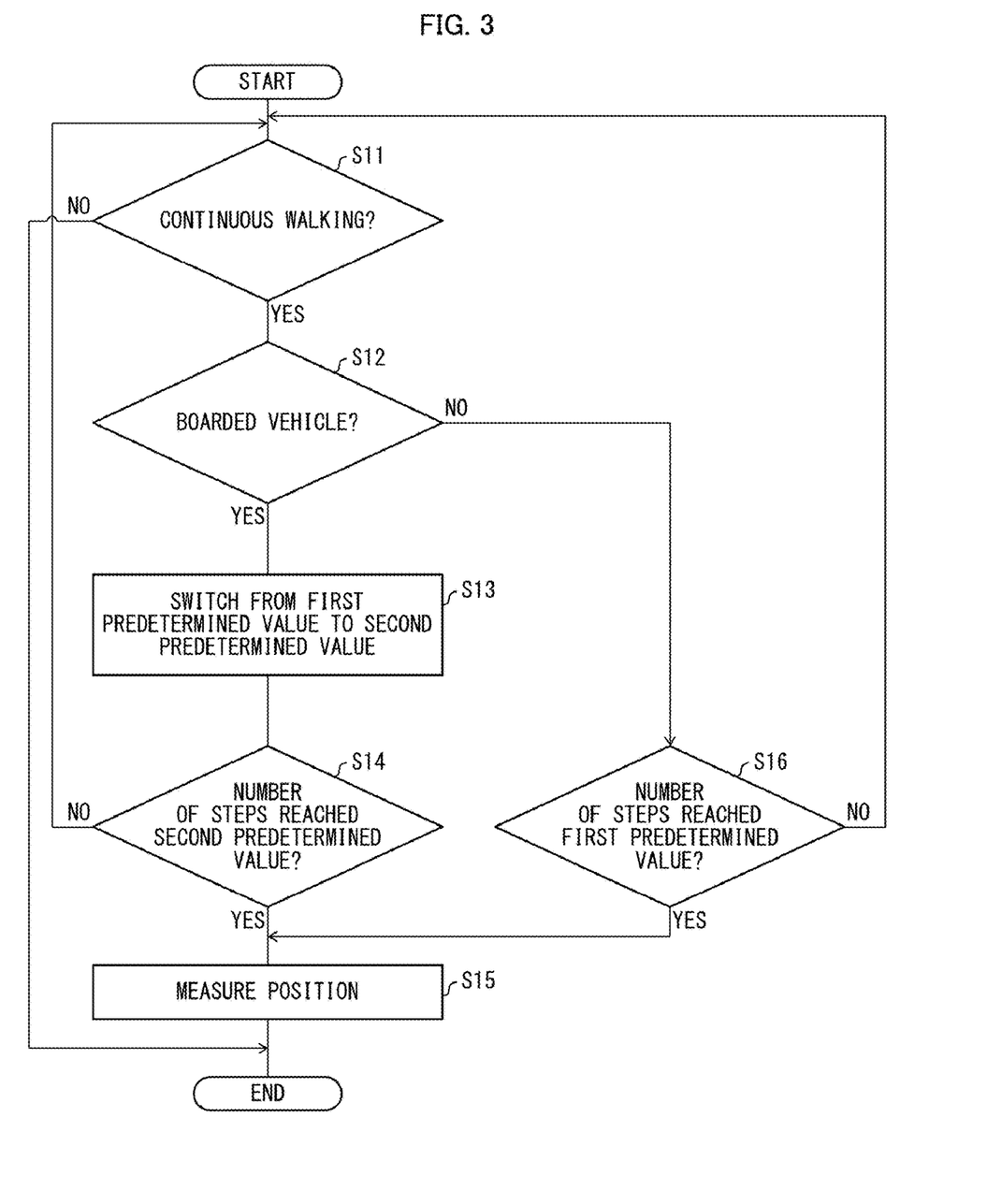
FIG. 3 is a flowchart showing a flow of a position measurement process carried out by the electronic device.

The following description will discuss, with reference to FIGS. 1 through 3, Embodiment 1 of the present invention.

(Configuration of Mobile Terminal)

FIG. 1 is a block diagram schematically illustrating a configuration of an electronic device 1 in accordance with Embodiment 1. The electronic device 1 obtains positional information of a user and notifies the user of, for example, action information which indicates a position at which the user boarded a vehicle, a position at which the user exited the vehicle, and a route traveled by the user.

As illustrated in FIG. 1, the electronic device 1 includes a sensor section 2, a GPS receiving section 4, a display section 5, a position measurement instructing section 10, and a host control section 20. The position measurement instructing section 10 and the host control section 20 are realized by respective different circuits. The electronic device can control supply of electric power to the position measurement instructing section 10 and supply of electric power to the host control section 20 independently of each other. This allows the electronic device 1 to bring the position measurement instructing section 10 arid the host control section 20 into an activated mode or a sleep mode (hibernation) independently of each other. In other words, the position measurement instructing section 10 serves, for example, as a sensor microcomputer or the like which integrates and processes sensor values from a plurality of sensors. As such, when performing a predetermined process, the position measurement instructing section 10 does not need the host control section 20 executed by a CPU (Central Processing Unit), and is therefore capable of operating without involvement of the CPU. The predetermined process will be detailed later.

The electronic device 1 may be, for example, an electronic device such as a smartphone, a mobile phone, a laptop PC, a tablet terminal, an c-book reader, or a PDA.

The sensor section 2 includes sensors such as an acceleration sensor 2a, a gyroscopic sensor 2b, and a geomagnetic sensor 2c. The sensor section 2 detects a walking action of the user. Specifically, the sensor section 2 generates a walk detection signal indicative of the walking action, and transmits the walk detection signal thus generated to a continuous walk detecting section 11 and a step counting section 13 (each of which will be described later). The sensor section 2 may be constituted by a well-known sensor capable of detecting the walking action of the user. As such a sensor section 2, it is possible to use, for example, the acceleration sensor 2a and the like capable of detecting a three-dimensional movement of the user.

The sensor section 2 detects a sensor value corresponding to a traveling state of the user who carries the electronic device 1 around while traveling. The sensor value corresponding to the traveling state indicates, for example, a change in acceleration, traveling speed, oscillation pattern, or inclination regarding the electronic device 1, and the sensor section 2 can use a single one or a combination of the acceleration, gyroscopic, geomagnetic, and other type of sensors 2a, 2b, and 2c. The sensor section 2 supplies, to a boarding determining section 12, the sensor value corresponding to the traveling state of the user.

The GPS receiving section 4 receives radio waves from a GPS (global positioning system), arid supplies a GPS signal thus received to a positional information obtaining section 21 of the host control section 20.

The display section 5 receives display data from the host control section 20, and displays a display content on a display screen on the basis of the display data thus received. Specifically, the display section 5 includes, for example, (i) a display element such as an LCD (Liquid Crystal Display) or an EL (Electroluminescence) display and (ii) a driver circuit which drives the display element on the basis of the display data received.

(Details of Position Measurement Instructing Section)

The position measurement instructing section 10 includes the continuous walk detecting section 11, the hoarding determining section 12, the step counting section 13, a frequency switching section 14, and a frequency setting section 15.

The continuous walk detecting section 11 detects continuous walking of the user. Specifically, the continuous walk detecting section 11 determines whether or not the user has been continuously walking by determining, for example, whether or not the user stopped for not shorter than a certain time period within a period during which the user last took a predetermined number of steps. In a case where the continuous walk detecting section 11 detects continuous walking of the user, the continuous walk detecting section 11 supplies a continuous walk detection signal to the hoarding determining section 12.

In a case where the continuous walk detection signal is supplied from the continuous walk detecting section 11, the boarding determining section 12 determines, on the basis of the sensor value corresponding to the traveling state and supplied from the sensor section 2, whether or not the user has boarded or exited a vehicle. The boarding determining section 12 decides, for example, whether or not the user has boarded a vehicle such as a train (railway), an automobile, a ship, or an airplane as well as whether or not the user has exited the vehicle. With use of a well-known technique, the boarding determining section 12 can identify the user's boarding or exiting a vehicle on the basis of the sensor value from the sensor section 2. For example, on the basis of a degree of acceleration and/or a cycle of change in acceleration, the boarding determining section 12 can determine whether the user is on board a vehicle or walking, etc., and thus can identify the user's boarding or exiting a vehicle. Upon determining that the user has boarded or exited a vehicle, the boarding determining section 12 supplies a boarding determination signal to the frequency switching section 14.

The step counting section 13 counts the number of steps taken by the user on the basis of the walk detection signal from the sensor section 2. Specifically, the step counting section 13 (i) generates, from the walk detection signal generated by the sensor section 2, step count data indicative of the number of steps and (ii) transmits the step count data to the frequency setting section 15.

In a case where the boarding determining section 12 determines that the user has boarded or exited a vehicle, the frequency switching section 14 switches a frequency, at which the positional information obtaining section 21 obtains the positional information, from a first frequency, which had been set before the user boarded the vehicle, to a second frequency. Specifically, for example, in a case where the frequency switching section 14 receives, from the boarding determining section 12, a boarding determination signal indicating that the user has boarded a vehicle, the frequency switching section 14 switches the frequency, which is set in the frequency setting section 15 and at which the positional information obtaining section 21 obtains the positional information, from the first frequency, which had been set before the user boarded the vehicle, to the second frequency.

The frequency setting section 15 supplies, to the positional information obtaining section 21 (described later) and in accordance with the frequency which has been set, position measurement instruction for instructing to obtain the positional information. Until the frequency is switched by the frequency switching section 14, that is, while the user is traveling by walk before boarding the vehicle, the frequency at which the positional information obtaining section 21 obtains the positional information is set to the first frequency in the frequency setting section 15.

Further, in a case where the first frequency is set in the frequency setting section 15 as the frequency at which the positional information obtaining section 21 obtains the positional information, the frequency setting section 15 supplies the position measurement instruction every time the number of steps counted by the step counting section 13 reaches a first predetermined value. In a case where the second frequency is set in the frequency setting section 15 as the frequency at which the positional information obtaining section 21 obtains the positional information, the frequency setting section 15 supplies the position measurement instruction every time the number of steps counted by the step counting section 13 reaches a second predetermined value.

(Host Control Section)

The host control section 20 includes the positional information obtaining section 21 and a notifying section 22. The host control section 20 is constituted by one or more circuits. The host control section 20 includes a CPU (Central Processing Unit), a ROM (Read Only Memory), a RAM (Random Access Memory), and the like. The CPU executes a program stored in the ROM, the RAM, or the like, so that the host control section 20 controls sections of the electronic device 1.

The positional information obtaining section 21 obtains the positional information of the user. Specifically, in a case where the position measurement instruction is supplied from the frequency setting section 15, the positional information obtaining section 21 identifies a current position of the electronic device 1, i.e., the user, on the basis of the GPS signal supplied from the GPS receiving section 4. The positional information obtaining section 21 is not limited to one which uses GPS, provided that the positional information obtaining section 21 is capable of identifying (a range of) the current position of the user (electronic device 1). For example, the positional information obtaining section 21 may be configured to (i) receive, from a communication section 19, information (a cell ID (identifier)) of a base station, information of a Wi-Fi (registered trademark) access point, and/or information from a beacon which performs BLE (Bluetooth Low Energy (registered trademark)) communications and (ii) identify the current position on the basis of these pieces of information. Upon obtaining the positional information of the user, the positional information obtaining section 21 supplies the result to the notifying section 22.

The notifying section 22 causes the display section 5 to display the positional information of the user supplied from the positional information obtaining section 21.

(Setting of Frequency)

The following describes, with reference to FIG. 2, an example of setting of the first frequency and the second frequency. FIG. 2 is a view for explaining an overview of position measurement carried out by the electronic device 1. (a) of FIG. 2 illustrates position measurement carried out by a conventional electronic device, and (b) of FIG. 2 illustrates position measurement carried out by the electronic device 1.

In the electronic device 1, as described above, the frequency at which the positional information obtaining section 21 obtains the positional information of the user (carries out position measurement of measuring the position of the user) with use of GPS or the like can be determined in accordance with the number of steps taken by the user. In this case, setting the frequency of the position measurement to every small number of steps causes the position measurement to be carried out frequently. This increases power consumption of the electronic device 1. It is therefore preferable to set the frequency of the position measurement, for example, to every several hundred steps.

However, in a case where the user boards or exits the vehicle, keeping the frequency of the position measurement set to every several hundred steps may result in no position measurement carried out when the user exits the vehicle, since the number of steps may not have reached several hundred when the user exits the vehicle. For example, in a case where the user boards a train and position measurement at the time when the user exits the train cannot be carried out because the number of steps has not reached several hundred, there may be such problems that positional accuracy of a station at which the user exited the train is compromised or it is impossible to know at which station the user exited the train, clue to a failure to identify a position at which the user exited the train. Further, for example, in a case where the user boards an automobile and a parking lot for the automobile is located close to the user's home, there may be a problem that the user's arrival at home is not determined because the number of steps taken by the user after the user exited the automobile is small.

This is described more specifically with reference to an example in which, as illustrated in (a) and (b) of FIG. 2, the user travels a route which extends from a place P1, at which the user starts walking, to the user's home H through a place P2, which is 300 steps forward from the place P1, a place P3, which is another 300 steps forward from the place P2, a boarding place P4, at which the user boards an automobile, and an exit place P5, at which the user exits the automobile. Note, here, that the electronic device 1 is set to the first frequency of the position measurement so that the position measurement is carried out every time the number of steps taken by the user reaches 300 steps.

In a case where the frequency of the position measurement is set in a conventional electronic device, the first frequency of the position measurement is unchanged. This case will be detailed below. As illustrated in (a) of FIG. 2, a position of the user is measured at the place P2 and the place P3. The position measurement may be carried out at the boarding place P4 in a case where the boarding determining section 12 determines that the user has boarded the vehicle.

Between the boarding place P4 and the exit place P5, the user hardly walks because the user is on board the automobile. Accordingly, the number of steps traveled by the user does not reach 300 steps, and measurement of a position of the user is not carried out at the exit place P5. Further, for example, in a case where a distance between the exit place P5 and the user's home H is as small as approximately 20 steps away, the number of steps traveled does not reach 300 steps, even if the number of steps traveled from the boarding place P4 is taken into account. Accordingly, even in a case where the user's home is a destination, the position measurement may not be carried out at the destination and, accordingly, it may not be determined that the user has arrived at the destination.

In contrast, in the electronic device 1 in accordance with Embodiment 1, the frequency switching section 14 switches the frequency of the position measurement from the first frequency to the second frequency, in a case where it is decided that the user has boarded the vehicle. This case will be detailed below. As illustrated in (b) of FIG. 2, the electronic device 1 carries out measurement of a position of the user at the place P2 and the place P3. The position measurement may be carried out at the boarding place P4 in a case where the boarding determining section 12 determines that the user has boarded the vehicle. It is also possible to employ a configuration in which, although the position measurement is not carried out in accordance with walking, (i) monitoring is performed periodically by setting a timer in the sensor microcomputer in order to know a position of the user and a notification, which is given from the sensor microcomputer in a case where the sensor value from the sensor section 2 changes, is used as a trigger for the position measurement.

In a case where the boarding determining section 12 determines, at the boarding place P4, that the user has boarded the automobile, the number of steps according to which a frequency of the position measurement is determined is switched by the frequency switching section 14 from 300 steps (the first frequency, the first predetermined value) to, for example, 20 steps (the second frequency, the second predetermined value).

It can be assumed, here, that the user takes approximately 20 steps when the user exits the automobile. In view of this, a frequency of the position measurement after the boarding of the user is set to 20 steps, so that positional information is obtained after 20 steps of walking is detected after it is determined that the user has boarded or exited the vehicle. This allows accurately knowing a position at which the user exited the automobile. Further, it also becomes possible to decide positional information of the destination (the use home) even in a case where a distance between the exit place P5 and the user's home (destination) is as small as 20 steps away. Thus, by setting the second frequency higher than the first frequency, it becomes possible to realize the electronic device 1 which not only is capable of measuring an accurate position of a user when the user exits a vehicle but also achieves a reduction in power consumption.

Further, the electronic device 1 may be configured to detect when the number of steps detected reaches the second predetermined value, that the user has exited the vehicle.

In this case, the frequency at which the positional information obtaining section 21 obtains positional information may be switched from the second frequency to the first frequency, after the positional information obtaining section 21 obtains positional information at the second frequency. In other words, it is possible to employ a configuration in which (i) position measurement at the second frequency (position measurement carried out every time 20 steps are taken) is valid only once after it is determined that the user has boarded the vehicle and after the position measurement at the second frequency is carried out, the frequency switching section 14 switches the frequency of the position measurement to the first frequency (300 steps). This allows (i) accurately measuring, at a short interval of measurement, a position at which the user exited the vehicle and then increasing the interval of measurement again. This enables a reduction in power consumption. Thereafter, in a case where it is determined that the user has boarded a vehicle again, the frequency switching section 14 may switch the frequency, at which positional information of the user is obtained, from the first frequency to the second frequency again.

In a case where, for example, the first frequency is set to every 300 steps (the first predetermined value), the position measurement is carried out approximately every 2 minutes to 3 minutes. This allows the number of times positional information is obtained to be reduced during a normal walk by the user, so that a reduction in power consumption is achieved. As for positional information, the configuration above allows obtaining positional information approximately every 200 meters, which is not problematic in terms of accuracy of positional information of GPS or the like.

Further, in a case where, for example, the second frequency is set to every 20 steps (the second predetermined value), the position measurement is carried out approximately every 10 seconds. This allows a position at which the user exits the vehicle to be accurately identified on the basis of walking and, accordingly, enables an improvement in accuracy of measurement of the position at which the user exits the vehicle. Further, in a case where the user can return to the user's home from the parking lot by 20 steps to 30 steps, accurate determination of the user's home also becomes possible.

In Embodiment 1, the description above has discussed a case in which the second frequency is higher than the first frequency. Note, however, that Embodiment 1 is not limited to such a case, and the second frequency may be lower than the first frequency. For example, in a case where the user always uses a station of a subway etc. at which station a position of the user cannot be measured by GPS when the user exits the train, setting the second frequency to be higher than the first frequency causes an increase in power consumption because the position measurement is carried out frequently until positional information is obtained. This problem can be avoided, for example, by setting the second predetermined value of the second frequency to 500 steps so that the position measurement is carried out at tinning when the user goes up to the ground level after exiting the train. This enables a reduction in power consumption. In other words, the second frequency may be set by the user in accordance with an action pattern of the user. It is also possible to employ a configuration in which (i) a position, measurement of which failed a plurality of times, is learned and (ii) the setting of the second frequency is changed, accordingly.

(Example of Position Measurement Process)

FIG. 3 is a flowchart showing a flow of a position measurement process carried out by the electronic device 1. The process shown in FIG. 3 is carried out (i) in a case where activation of the electronic device 1 is completed and the sensor section 2 detects walking or (ii) every predetermined time period. First, the continuous walk detecting section 11 determines whether or not walking detected is continuous walking (S11, boarding determining step). In a case where the walking detected by the sensor section 2 is continuous walking (YES at S11), the boarding determining section 12 determines whether or not the user has boarded a vehicle (S12). In a case where the user has boarded a vehicle (YES at S12), the frequency switching section 14 switches timing, which is set in the frequency setting section 15 arid at which the positional information obtaining section 21 obtains positional information, from the first frequency to the second frequency. That is, the frequency switching section 14 switches a value, which has been set, of the number of steps from the first predetermined value to the second predetermined value (S13, frequency switching step). Subsequently, the frequency setting section 15 determines whether or not the number of steps counted by the step counting section 13 has reached the second predetermined value (S14). In a case where the number of steps counted by the step counting section 13 has reached the second predetermined value (YES at S14), the frequency setting section 15 causes the positional information obtaining section 21 to obtain positional information. In other words, the electronic device 1 measures a position of the user (S15, positional information obtaining step).

In a case where the user has not boarded a vehicle (NO at S12), the tinning which is set in the frequency setting section 15 and at which the positional information obtaining section 21 obtains positional information is the first frequency. Accordingly, the frequency setting section 15 determines whether or not the number of steps counted by the step counting section 13 has reached the first predetermined value (S16). In a case where the number of steps counted by the step counting section 13 has reached the first predetermined value (YES at S16), the frequency setting section 15 causes the positional information obtaining section 21 to obtain positional information (S15)

In a case where the walking detected by the sensor section 2 is not continuous walking (NO at S11), the process is ended. In a case where the number of steps counted by the step counting section 13 has not reached the second predetermined value (NO at S14), the process returns to S11. In a case where the number of steps counted by the step counting section 13 has not reached the first predetermined value (NO at S16), the process returns to S11.

The description above has discussed a case in which, when the user has boarded a vehicle, a frequency at which positional information is obtained is changed from the first frequency, which had been set before the user boarded the vehicle, to the second frequency. Note, however, that it is possible to employ a configuration in which a frequency at which positional information is obtained is switched from the first frequency to the second frequency when the user has exited a vehicle.

[Embodiment 2]

Figure 4:
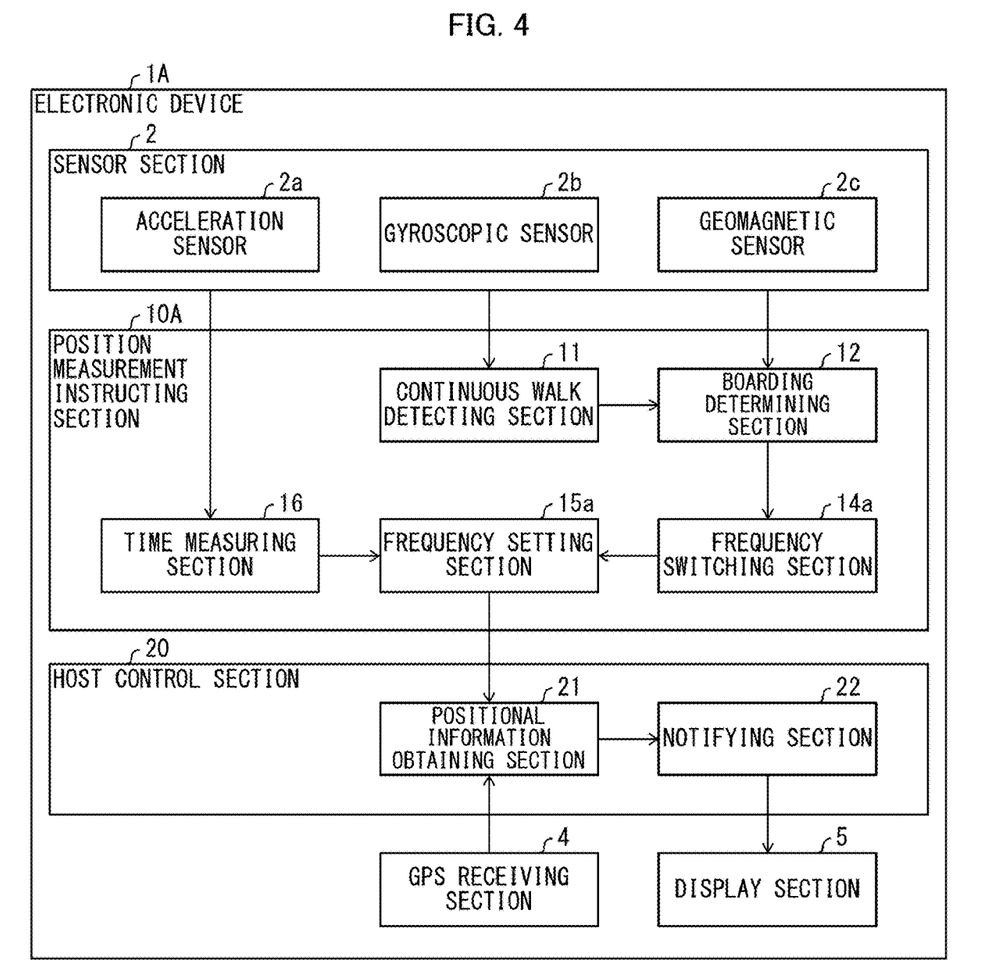
FIG. 4 is a functional block diagram schematically illustrating a configuration of an electronic device in accordance with Embodiment 2 of the present invention.
Figure 5:
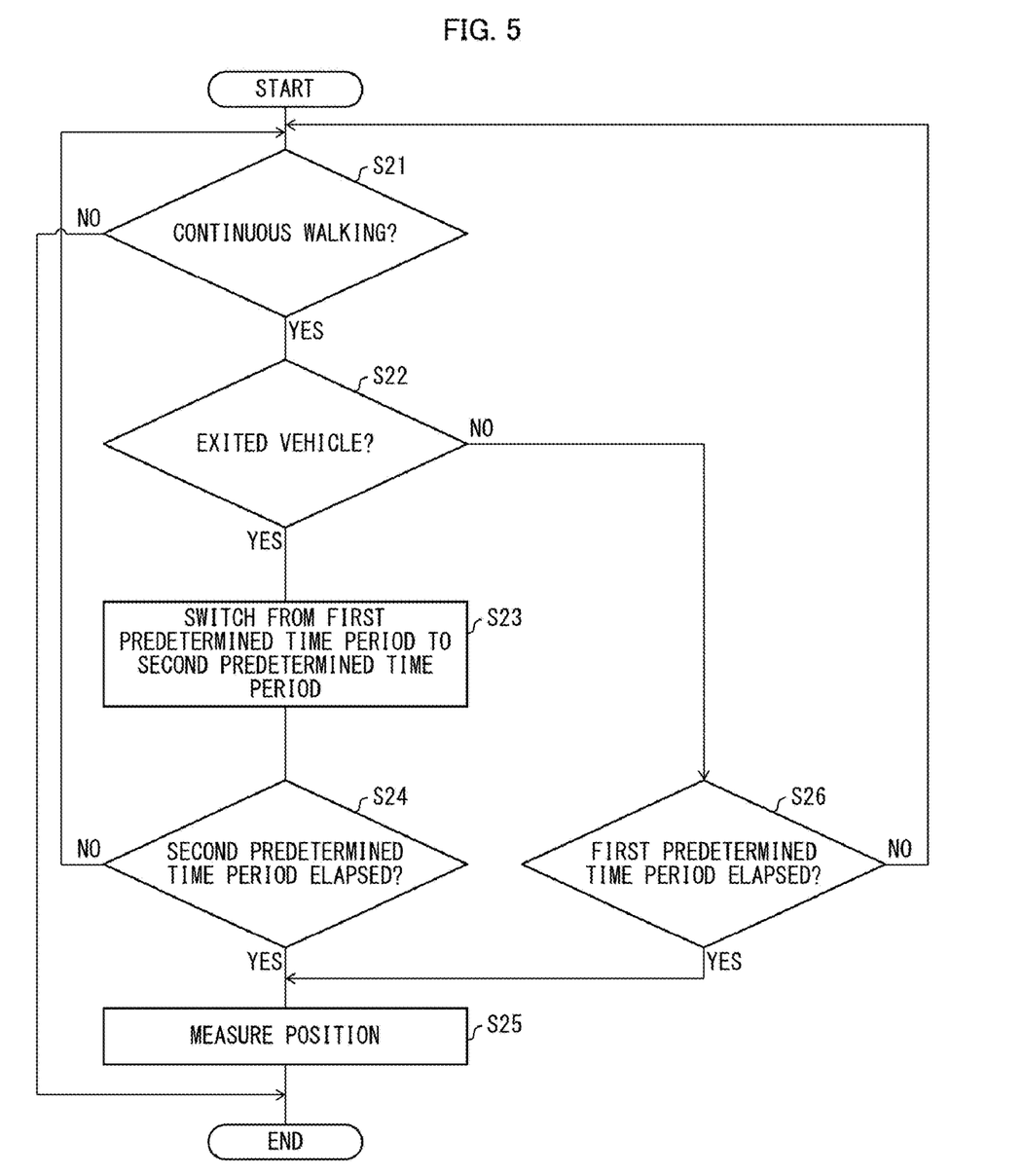
FIG. 5 is a flowchart showing a flow of a position measurement process carried out by the electronic device.

The following description will discuss, with reference to FIGS. 4 and 5, Embodiment 2 of the present invention. FIG. 4 is a functional block diagram schematically illustrating a configuration of an electronic device 1A in accordance with Embodiment 2 of the present invention. The electronic device 1A illustrated in FIG. 4 has the same configuration as that of the electronic device 1 except that the electronic device 1A includes a position measurement instructing section 10A in place of the position measurement instructing section 10.

(Details of Position Measurement Instructing Section)

As illustrated in FIG. 4, the position measurement instructing section 10A differs from the position measurement instructing section 10 in that the position measurement instructing section 10A includes a time measuring section 16, a frequency switching section 14a, and a frequency setting section 15a in place of the step counting section 13, the frequency switching section 14, and the frequency setting section 15.

The time measuring section 16 measures time. Specifically, in a case where a sensor section 2 detects walking of a user, the time measuring section 16 starts measuring time.

In a case where the frequency switching section 14a receives, from a boarding determining section 12, a boarding determination signal indicating that the user has exited a vehicle, the frequency switching section 14a switches a frequency, which is set in the frequency setting section 15a and at which a positional information obtaining section 21 obtains positional information, from a first frequency, which had been set before the user boarded the vehicle, to a second frequency.

In accordance with the frequency set, the frequency setting section 15a supplies, to the positional information obtaining section 21, a position measurement instruction for instructing to obtain positional information. Until the frequency is switched by the frequency switching section 14a, that is, while the user is traveling by walk before boarding the vehicle, the frequency at which the positional information obtaining section 21 obtains the positional information is set to the first frequency in the frequency setting section 15a.

In a case where the first frequency is set in the frequency setting section 15a as the frequency at which the positional information obtaining section 21 obtains positional information, the frequency setting section 15a supplies the position measurement instruction every first predetermined time period. In a case where the second frequency is set in the frequency setting section 15a as the frequency at which the positional information obtaining section 21 obtains positional information, the frequency setting section 15a supplies the position measurement instruction every second predetermined time period.

The first predetermined time period and the second predetermined time period are not particularly limited. For example, setting the first predetermined time period to be long causes the position measurement to be carried out less frequently, so that a decrease in power consumption is achieved. Setting the second predetermined time period to be short allows accurately obtaining a position at which the user exits a vehicle.

(Example of Position Measurement Process)

FIG. 5 is a flowchart showing a flow of a position measurement process carried out by the electronic device 1A. The process shown in FIG. 5 is carried out in a case where activation of the electronic device 1 is completed and the sensor section 2 detects walking. First, a continuous walk detecting section 11 determines whether or not walking detected is continuous walking (S21). In a case where the walking detected by the sensor section 2 is continuous walking (YES at S21), the boarding determining section 12 determines whether or not the user has exited a vehicle (S22). In a case where the user has exited a vehicle (YES at S22), the frequency switching section 14a switches timing, which is set in the frequency setting section 15a and at which the positional information obtaining section 21 obtains positional information, from the first frequency to the second frequency. That is, the frequency switching section 14a switches a time period, which has been set, from the first predetermined time period to the second predetermined time period (S23). Subsequently, the frequency setting section 15a determines whether or not a time period measured by the time measuring section 16 has reached the second predetermined time period (S24). In a case where the time period measured by the time measuring section 16 has reached the second predetermined time period (YES at S24), the frequency setting section 15a causes the positional information obtaining section 21 to obtain positional information. In other words, the electronic device 1A measures a position of the user (S25).

In a case where the user has not exited a vehicle (NC) at S22), the timing which is set in the frequency setting section 15a and at which the positional information obtaining section 21 obtains positional information is the first frequency. Accordingly, the frequency setting section 15a determines whether or not the time period measured by the time measuring section 16 has reached the first predetermined time period (S26). In a case where the time period measured by the time measuring section 16 has reached the first predetermined time period (YES at S26), the frequency setting section 15a causes the positional information obtaining section 21 to obtain positional information (S25).

In a case where the walking detected by the sensor section 2 is not continuous walking (NO at S21), the process is ended. In a case where the tune period measured by the time measuring section 16 has not reached the second predetermined time period (NO at S24), the process returns to S21. In a case where the time period measured by the time measuring section 16 has not reached the first predetermined time period (NO at S26), the process returns to S21.

The description above has discussed a case in which, when the user has boarded a vehicle, a frequency at which positional information is obtained is changed from the first frequency, which had been set before the user exited the vehicle, to the second frequency. Note, however, that it is possible to employ a configuration in which a frequency at which positional information is obtained is switched from the first frequency to the second frequency when the user has boarded a vehicle.

MODIFIED EXAMPLE

The following description will discuss a modified example of Embodiment 2 of the present invention. In the modified example, the boarding determining section 12 may be configured to (i) determine, in accordance with a sensor value which is supplied from the sensor section 2 and corresponds to a traveling state, whether or not a user has boarded a vehicle and (ii) further determine whether or not the user is in an on-board traveling state in which the user is traveling on board the vehicle (the vehicle on board which the user is traveling). In other words, the boarding determining section 12 further determines whether or not the user is in the on-board traveling state in which (i) the user is on board a vehicle and the vehicle is traveling. A state (a state other than the on-board traveling state) which is not the on-board traveling state is, for example, a state in which the user has stopped without boarding a vehicle, a state in which the user is walking, a state in which the user is about to board a vehicle, or a state in which the user is about to exit a vehicle.

Specifically, the boarding determining section 12 (i) obtains, every predetermined time period, a sensor value supplied from the sensor section 2 and corresponding to a traveling state of the user and (ii) determines whether or not the user is in the on-board traveling state in consideration of overall sensor values which were obtained over a certain time period and each of which corresponds to a traveling state.

In the modified example, in a case where the boarding determining section 12 determines that the user has boarded a vehicle and further determines that the user is in the on-board traveling state, the frequency switching section 14a switches a frequency, which is set in the frequency setting section 15a and at which the positional information obtaining section 21 obtains positional information, from a frequency which was last set (for example, the first frequency or the second frequency) to another frequency (a third frequency). In a case of obtaining positional information at the third frequency, the positional information obtaining section 21 obtains positional information every third predetermined time period. The third frequency may be, for example, a frequency at which no positional information is obtained or a frequency which is lower than the first frequency. This allows further reducing a frequency of position measurement in a case where the user is traveling on board a vehicle and, accordingly, allows achieving a further reduction in power consumption.

Further, in a case where the boarding determining section 12 determines that the user is in a state other than the on-board traveling state, the frequency switching section 14a switches a frequency, which is set in the frequency setting section 15a and at which the positional information obtaining section 21 obtains positional information, from a frequency which was last set (for example, the first frequency or the third frequency) to the second frequency. This allows the position measurement to be carried out at the second frequency in a case where the user is not in the on-board traveling state after boarding the vehicle. Accordingly, for example, a position at which the vehicle has stopped can be measured accurately. Further, since a state in which the user is exiting a vehicle also falls under the state other than the on-board traveling state, it is possible to carry out, also when the user exits the vehicle, the position measurement at the second frequency. This enables accurate measurement of a position at which the user exits the vehicle.

Note, here, that the frequency switching section 14a may be configured, for example, to (i) switch a frequency, at which the positional information obtaining section 21 obtains positional information, from the first frequency to the third frequency when the boarding determining section 12 determines that the user has boarded a vehicle and (ii) then switch the frequency to the second frequency when the hoarding determining section 12 determines that the user has exited the vehicle. This case, however, has a problem that accurate detection of the user's exiting the vehicle is not possible in a case where the boarding determining section 12 erroneously determines that the user has exited the vehicle.

In view of this, the hoarding determining section 12 may be configured such that after determining that the user has boarded a vehicle, the boarding determining section 12 determines that the user has exited the vehicle in a case where a state in which the on-board traveling state is not detected continues for a certain time period. This allows preventing the boarding determining section 12 from erroneously determining that the user has exited the vehicle. Accordingly, accurate detection of the user's exiting the vehicle becomes possible.

More specifically, the frequency switching section 14a may be configured, for example, to (i) switch the frequency, at which the positional information obtaining section 21 obtains positional information, from the first frequency to the third frequency in a case where it is determined that the user has boarded a vehicle and (ii) then switch the frequency to the second frequency when the boarding determining section 12 determines that the user has exited the vehicle in a case where a state in which the on-board traveling state is not detected continues for a certain time period.

Further, the electronic device 1A may carry out the position measurement at such a frequency that (i) in a case where the boarding determining section 12 determines that the user has boarded a vehicle, the frequency at which the positional information obtaining section 21 obtains positional information is switched from the first frequency to a fourth frequency and (ii) in a case where the boarding determining section 12 determines that the user has exited the vehicle, the frequency at which the positional information obtaining section 21 obtains positional information is switched from the fourth frequency to the second frequency. In a case of obtaining positional information at the fourth frequency, the positional information obtaining section 21 obtains positional information every fourth predetermined time period. In this case, for example, by setting the fourth frequency to be longer than the first frequency, it is possible to achieve a further reduction in power consumption.

[Software Implementation Example]

The position measurement instructing sections 10 and 10A (e.g., the continuous walk detecting section 11, the boarding determining section 12, the step counting section 13, the frequency switching sections 14 and 14a, the frequency setting sections 15 arid 15a, and the time measuring section 16) and the host control section 20 (e.g., the positional information obtaining section 21 and the notifying section 22) of the electronic devices 1 and 1A may be realized by a logic circuit (hardware) provided in an integrated circuit (IC chip) or the like or may be realized by software as executed by a CPU (Central Processing Unit).

In the latter case, each of the electronic devices 1 and 1A includes: a CPU that executes instructions of a program that is software realizing the foregoing functions; ROM (Read Only Memory) or a storage device (each referred to as "storage medium") storing the program and various kinds of data in such a form that they are readable by a computer (or a CPU); and RAM (Random Access Memory) that develops the program in executable form. The object of the present invention can be achieved by a computer (or a CPU) reading and executing the program stored in the storage medium. The storage medium may be "a non-transitory tangible medium" such as a tape, a disk, a card, a semiconductor memory, and a programmable logic circuit. Further, the program may be made available to the computer via any transmission medium (such as a communication network and a broadcast wave) which enables transmission of the program. Note that the present invention can also be implemented by the program in the form of a computer data signal embedded in a carrier wave which is embodied by electronic transmission.

[Recap]

Electronic devices (1 and 1A) in accordance with Aspect 1 of the present invention are each an electronic device including: a positional information obtaining section (21) for obtaining positional information of a user; a boarding determining section (12) for determining whether or not the user has boarded or exited a vehicle; and a frequency switching section (14 or 14a) for switching a frequency, at which the positional information obtaining section obtains the positional information, from a first frequency to a second frequency in a case where the boarding determining section determines that the user has boarded or exited the vehicle, the first frequency being a frequency which had been set before the user boarded the vehicle.

According to the configuration above, before the user boards the vehicle, the positional information of the user is obtained by the positional information obtaining section at the first frequency. As such, for example, by setting the first frequency low, it is possible to prevent the positional information to be frequently obtained. This enables a reduction in power consumption. Further, when the boarding determining section determines that the user has boarded or exited the vehicle, the frequency switching section switches the frequency, at which the positional information obtaining section obtains the positional information of the user, from the first frequency to the second frequency. As such, for example, by setting the second frequency low, it is possible to know, for example, information of a position at which the user exited the vehicle. This allows providing an electronic device which not only is capable of measuring an accurate position of the user when the user exits a vehicle but also achieves a reduction in power consumption.

In Aspect 2 of the present invention, the electronic device (1) in accordance with Aspect 1 is preferably configured such that the electronic device (1) further includes a step counting section (13) for counting the number of steps taken by the user, wherein: the frequency switching section (14) switches the frequency, at which the positional information obtaining section (21) obtains the positional information, from the first frequency to the second frequency in a case where the boarding determining section (12) determines that the user has boarded or exited the vehicle; and the positional information obtaining section (i) obtains, in a case of obtaining the positional information at the first frequency, the positional information every time the number of steps counted by the step counting section reaches a first predetermined value and (ii) obtains, in a case of obtaining the positional information at the second frequency, the positional information every time the number of steps counted by the step counting section reaches a second predetermined value.

According to the configuration above, for example, in a case where the first predetermined value is set to 300 steps, the position measurement is carried out once every 2 minutes to 3 minutes when, for example, the user is in a walking state. This allows preventing the position measurement to be carried out frequently and, accordingly enables a reduction in power consumption.

Further, it can be assumed that the user takes approximately 20 steps when the user exits the vehicle. In view of this, for example, the second predetermined value is set to 20 steps, so that positional information is obtained after 20 steps of walking is detected after it is determined that the user has boarded or exited the vehicle. This allows accurately knowing a position at which the user exited the automobile. Further, it also becomes possible to decide positional information of a destination accurately even in a case where the destination is reachable by a small number of steps from a place at which the user exited the vehicle.

In Aspect 3 of the present invention, the electronic device (1) in accordance with. Aspect 1 or 2 is preferably configured such that the second frequency is higher than the first frequency.

According to the configuration above, the first frequency is set to be lower than the second frequency. This allows preventing the positional information from being obtained frequently when user has not boarded the vehicle and, accordingly, enables a reduction in power consumption. Further, since the second frequency is set to be higher than the first frequency, it is possible to obtain the positional information frequently when the user exits the vehicle. This allows accurately measuring a place in which the user exits the vehicle.

In Aspect 4 of the present invention, the electronic device (1A) in accordance with Aspect 1 is preferably configured such that the frequency switching section (14a) switches the frequency, at which the positional information obtaining section (21) obtains the positional information, from the first frequency to the second frequency in a case where the boarding determining section (12) determines that the user has boarded or exited the vehicle; the positional information obtaining section obtains, in a case of obtaining the positional information at the first frequency, the positional information every first predetermined time period and obtains, in a case of obtaining the positional information at the second frequency, the positional information every second predetermined time period.

According to the configuration above, for example, by setting the first predetermined time period to be 2 minutes to 3 minutes, it is possible to prevent the position measurement from being carried out frequently. This enables a reduction in power consumption. Further, by setting the second predetermined time period to be 10 seconds, it becomes possible to carry out the position measurement frequently when the user exits the vehicle. This allows measuring an accurate position of the user when the user exits the vehicle.

In Aspect 5 of the present invention, the electronic device (1A) in accordance with Aspect 4 is preferably configured such that the boarding determining section (12) further determines whether or not the user is in an on-board traveling state in which the user is on board a vehicle and the vehicle is traveling; the frequency switching section (14a) switches the frequency, at which the positional information obtaining section (21) obtains the positional information, from a frequency, which was last set, to the second frequency in a case where the boarding determining section determines that the user has boarded the vehicle and further determines that the user is not in the on-board traveling state and switches the frequency, at which the positional information obtaining section obtains the positional information, from a frequency, which was last set, to a third frequency in a case where the boarding determining section determines that the user has boarded the vehicle and further determines that the user is in the on-board traveling state; and the positional information obtaining section obtains, in a case of obtaining the positional information at the third frequency, the positional information every third predetermined time period.

According to the configuration above, for example, setting the third frequency to be lower than the first frequency allows the position measurement to be carried out less frequently than the first frequency, in a case where the user is traveling on board the vehicle. This enables a further reduction in power consumption. Further, in a case where it is determined, after the user boards the vehicle, that the user is in a state other than the on-board traveling state, the position of the user can be measured at the second frequency. This allows accurately measuring, for example, a position at which the vehicle has stopped and a position at which the user exited the vehicle.

In Aspect 6 of the present invention, the electronic device (1A) in accordance with Aspect 4 is preferably configured such that the frequency switching section (14a) switches the frequency, at which the positional information obtaining section (21) obtains the positional information, from the first frequency to a fourth frequency in a case where the boarding determining section (12) determines that the user has boarded the vehicle and switches the frequency, at which the positional information obtaining section obtains the positional information, from the fourth frequency to the second frequency in a case where the boarding determining section determines that the user has exited the vehicle; and the positional information obtaining section obtains, in a case of obtaining the positional information at the fourth frequency, the positional information every fourth predetermined time period.

According to the configuration above, even in a case where the user is on board a vehicle, a further reduction in power consumption can be achieved by setting an appropriate time period as the fourth frequency.

In Aspect 7 of the present invention, the electronic devices (1 and 1A) in accordance with Aspect 7 are each preferably configured such that after the positional information obtaining section (21) obtains the positional information at the second frequency, the frequency switching section (14 or 14a) switches the frequency, at which the positional information obtaining section obtains the positional information, from the second frequency to the first frequency.

According to the configuration above, after the positional information obtaining section obtains the positional information at the second frequency, the frequency switching section switches the frequency, at which the positional information obtaining section obtains the positional information, from the second frequency to the first frequency. As such, for example, by setting the second frequency high and setting the first frequency low, it is possible to (i) measure accurately a place at which the user exited the vehicle and (ii) then increasing an interval of position measurement again. This enables a reduction in power consumption.

A control method, in accordance with. Aspect 8 of the present invention, for controlling the electronic devices (1 and 1A) is a method for controlling an electronic device, comprising the steps of: (a) obtaining positional information of a user; (h) determining whether or not the user has boarded or exited a vehicle; and. (c) switching, in a case where it is determined in the step (b) that the user has boarded or exited the vehicle, a frequency, at which the positional information is obtained in the step (a), from a first frequency to a second frequency, the first frequency being a frequency which had been set before the user boarded the vehicle.

The configuration above brings about advantageous effect similar to those provided by Aspect 1.

The electronic device according to the foregoing embodiments of the present invention may be realized by a computer. In this case, the present invention encompasses: a control program for the electronic device which program causes a computer to operate as the sections (software elements) of the electronic device so that the electronic device can be realized by the computer; and a computer-readable storage medium storing the control program therein.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

INDUSTRIAL APPLICABILITY

The present invention is applicable to a portable device such as a mobile phone, a tablet terminal, an e-book reader, or a PDA.

REFERENCE SIGNS LIST 1, 1A: electronic device
12: boarding determining section
13: step counting section
14, 14a: frequency switching section
21: positional information obtaining section

The invention claimed is:
1. An electronic device comprising:
a positional information obtaining section for obtaining positional information of a user;
a boarding determining section for determining whether or not the user has boarded or exited a vehicle;
a frequency switching section for switching a frequency, at which the positional information obtaining section obtains the positional information, from a first frequency to a second frequency in a case where the boarding determining section determines that the user has boarded or exited the vehicle, the first frequency being a frequency which had been set before the user boarded the vehicle; and
a step counting section for counting the number of steps taken by the user, wherein:
the frequency switching section switches the frequency, at which the positional information obtaining section obtains the positional information, from the first frequency to the second frequency in a case where the boarding determining section determines that the user has boarded or exited the vehicle; and
the positional information obtaining section (i) obtains, in a case of obtaining the positional information at the first frequency, the positional information every time the number of steps counted by the step counting section reaches a first predetermined value and (ii) obtains, in a case of obtaining the positional information at the second frequency, the positional information every time the number of steps counted by the step counting section reaches a second predetermined value.

2. The electronic device as set forth in claim 1, wherein after the positional information obtaining section obtains the positional information at the second frequency, the frequency switching section switches the frequency, at which the positional information obtaining section obtains the positional information, from the second frequency to the first frequency.

3. An electronic device comprising:
a positional information obtaining section for obtaining positional information of a user;
a boarding determining section for determining whether or not the user has boarded or exited a vehicle: and
a frequency switching section for switching a frequency, at which the positional information obtaining section obtains the positional information, from a first frequency to a second frequency in a case where the boarding determining section determines that the user has boarded or exited the vehicle, the first frequency being a frequency which had been set before the user boarded the vehicle,
wherein the second frequency is higher than the first frequency.

4. An electronic device comprising:
a positional information obtaining section for obtaining positional information of a user;
a boarding determining section for determining whether or not the user has boarded or exited a vehicle; and
a frequency switching section for switching a frequency, at which the positional information obtaining section obtains the positional information, from a first frequency to a second frequency in a case where the boarding determining section determines that the user has boarded or exited the vehicle, the first frequency being a frequency which had been set before the user boarded the vehicle, wherein
the frequency switching section switches the frequency, at which the positional information obtaining section obtains the positional information, from the first frequency to the second frequency in a case where the boarding determining section determines that the user has boarded or exited the vehicle; and the positional information obtaining section (i) obtains, in a case of obtaining the positional information at the first frequency, the positional information every first predetermined time period and (ii) obtains, in a case of obtaining the positional information at the second frequency, the positional information every second predetermined time period; wherein
the boarding determining section further determines whether or not the user is in an on-board traveling state in which the user is on board a vehicle and the vehicle is traveling;
the frequency switching section
switches the frequency, at which the positional information obtaining section obtains the positional information, from a frequency, which was last set, to the second frequency in a case where the boarding determining section determines that the user has boarded the vehicle and further determines that the user is not in the on-board traveling state and
switches the frequency, at which the positional information obtaining section obtains the positional information, from a frequency, which was last set, to a third frequency in a case where the boarding determining section determines that the user has boarded the vehicle and further determines that the user is in the on-board traveling state; and
the positional information obtaining section obtains, in a case of obtaining the positional information at the third frequency, the positional information every third predetermined time period.

5. The electronic device as set forth in claim 4, wherein:
the frequency switching section
switches the frequency, at which the positional information obtaining section obtains the positional information, from the first frequency to a fourth frequency in a case where the boarding determining section determines that the user has boarded the vehicle and
switches the frequency, at which the positional information obtaining section obtains the positional information, from the fourth frequency to the second frequency in a case where the boarding determining section determines that the user has exited the vehicle; and
the positional information obtaining section obtains, in a case of obtaining the positional information at the fourth frequency, the positional information every fourth predetermined time period.

* * * * *